United States Patent
Holbrook et al.

(10) Patent No.: US 6,894,786 B1
(45) Date of Patent: May 17, 2005

(54) PROCESS MONITOR

(75) Inventors: Mark Burton Holbrook, Dunblane (GB); William George Beckmann, Dunblane (GB); Jacques Andre Grange, Cardiff (GB)

(73) Assignee: Vorgem Limited, Dunblane (GB)

( * ) Notice: Subject to any disclaimer, the term of this patent is extended or adjusted under 35 U.S.C. 154(b) by 0 days.

(21) Appl. No.: 09/743,164

(22) PCT Filed: Jul. 12, 1999

(86) PCT No.: PCT/GB99/02082
§ 371 (c)(1),
(2), (4) Date: Jan. 5, 2001

(87) PCT Pub. No.: WO00/03232
PCT Pub. Date: Jun. 20, 2000

(30) Foreign Application Priority Data

Jul. 11, 1998 (GB) .............................................. 9815005
Nov. 11, 1998 (GB) .............................................. 9824676

(51) Int. Cl.[7] .............................. G01B 9/02; H01L 21/00
(52) U.S. Cl. ........................................... 356/454; 438/9
(58) Field of Search ................................ 356/450, 454, 356/519, 451; 438/9, 7

(56) References Cited

U.S. PATENT DOCUMENTS

| 5,225,888 | A | * | 7/1993 | Selwyn et al. .............. 356/454 |
| 5,290,383 | A | | 3/1994 | Koshimizu |
| 6,081,334 | A | * | 6/2000 | Grimbergen et al. ....... 356/499 |
| 6,221,679 | B1 | * | 4/2001 | Smith, Jr. et al. ............... 438/7 |

FOREIGN PATENT DOCUMENTS

| DE | 27 36 262 A1 | 3/1978 |
| GB | 1 569 939 | 6/1980 |
| WO | 98/07002 | 2/1998 |

* cited by examiner

Primary Examiner—Samuel A. Turner
Assistant Examiner—Patrick Connolly
(74) Attorney, Agent, or Firm—Drinker Biddle & Reath LLP

(57) ABSTRACT

A substrate is etched in a vacuum enclosure in a process which generates plasma light emission. The process is monitored by passing emitted light via a window, a thin film narrow band filter and a "Fabry-Perot" etalon to a detector. The output signal from the detector is analyzed by shape recognition techniques to derive a measure of the progress of the process. The shape recognition preferably makes use of digital filtering and comparison with reference data derived from the theoretical analysis or from a calibration run.

9 Claims, 8 Drawing Sheets

PROCESS MONITOR

This application is the U.S. national phase application of PCT International Application No. PCT/GB99/02082 filed Jul. 12, 1999.

This invention relates to the field of the deposition, removal or modification of thin films and/or substrate materials.

Thin films are commonly used to modify surface properties, and processes occurring in vacuum apparatus are commonly used to deposit/remove or modify these films and for some applications this modification extends to the underlying substrate material. Typical applications include the coating of optical components to improve their light transmission or reflection properties, the coating of composite materials to improve adhesion behaviour, the coating of semiconductors to introduce insulating, conducting or indeed other layers with specific electronic, optical, magnetic or mechanical properties, and the production of ultra-small three dimensional structures for use in sensors and computer based recording devices. Typically these films and structures will have dimensions from 1 $\mu$m to several hundred microns. Frequently the films are structured in stacks where there is a change in chemical composition from one layer to the next. Such stacks vary from the simplest of one material on top of another to several hundred different layers in sequence.

In order for these structures to carry out the function for which they have been designed these materials frequently have to be etched, deposited or, once having been deposited, have to be removed or transformed (eg annealed) wholly or partially with very great precision. This deposition or removal is frequently carried out under conditions of vacuum using temperature controlled environments and gas or gases excited into the plasma state. It is beneficial to carry out measurement in-situ of the deposition or removal. Such processes generate considerable quantities of electrical, thermal, optical, vibrational and Radio Frequency noise.

This invention improves the process control of these deposition, etch or modification processes under these inherently noisy and difficult conditions.

In this field it is already known that the light emitted from a plasma may be used to determine the composition of the active species and the chemical concentration occurring at any particular time (Goffered G. G., SPIE Vol 1392, p454–p459). The described technique of measurement for process control is preferred by many users over alternatives such as quartz crystal microbalance or resistivity measurements or the like in that it is non-invasive, but as indicated below, it suffers considerable problems with noise. Alternative non-invasive techniques such as laser reflectometry (JVSTE 12 (6)p3306 '94 and WO98/07002) exist but they demand the careful set up of a light source reflecting from the sample and can limit the geometry of the processing chamber or the location of ancillary equipment. Mass spectrometry provides an alternative but it has the disadvantage of requiring to extract a sample for analysis which has concomitant problems with individual lifetimes of particular chemical species.

In its simplest form the spectral emission method provides a convenient remote measurement technique so that if it is tuned selectively to measure the concentration of element 'A' and an etch process is occurring to remove films consisting predominantly of element 'B' placed on top of and obscuring a substrate consisting of element 'A', then when the etch reaches down through all of the overlying film the signal representative of element 'B' will fall to a very small value to be replaced by a signal representative of element 'A'. This idealised 'step change' in the signal is in principle very easy to detect and a simple level change algorithm will allow automatic detection of the breakthrough point and thus automation of the film removal process. The establishment of several tuned channels of measurement (which may be realised as individual channels or a multiplexing scheme) permits simultaneous measurement of a number of characteristic spectral outputs which can help in discrimination.

The above known art has the disadvantage that the signal change is frequently not a simple abrupt step. Furthermore pulsed processes are being used more commonly now in order to improve process efficiency. In addition the frequency profile of the signals themselves may form complex shapes with either a lot of fine detail (in the form of many lines) or alteratively with very little fine detail (in the form of a continuum). The nature of the physical situation is therefore such that the exact determination of a process endpoint achieving good run-reproducibility requires extensive calibration and a high level of skill on the part of the process technician setting up the process control using spectral emission from the plasma etch, deposition or surface modification process. It is the objective of this current invention to provide for improved process control using spectral emission from a plasma process.

During the process some skilled operators will examine the behaviour in time of the emitted light characteristic of a particular constituent component in the plasma in an attempt to compare it to the behaviour that they noted during the calibration procedure. This relies on the constant presence of the operator and is not repeatable between operators.

From one aspect the invention consists in a method of automatically determining the progress of plasma processing including continuously monitoring a predetermined frequency or frequency band of radiation emitted from or absorbed by the plasma, developing a graphical or numerical output corresponding to the level of emittance or absorption, and electronically comparing that output with a predicted output or predicted trend to provide an indication of the progress of the process.

From another aspect the invention consists in a process control system for controlling a plasma based process including means for continuously capturing a frequency limited sample of radiation from a plasma, a detector for producing an output indicative of the time varying intensity of the radiation, and shape recognition means for comparing the output against a predicted output or trend to provide an indication of the progress of the process.

From another aspect the invention consists in a process control system for controlling a plasma based process including means for continuously capturing a predetermined range of frequencies and prior to conversion to an electrical signal using a shape recognition means to identify characteristic shapes in the spectral domain. The refined signal is then incident on a detector means for producing an output which is indicative of the time varying intensity. A shape recognition means is then employed in the time domain for comparing the output against a predicted output or trend to provide an indication of the progress of the process.

From another aspect the invention consists in a process control system for controlling a plasma based process including means for continuously capturing a predetermined range of frequencies and after their incidence on a detector means using a shape recognition means to identify characteristic shapes in the spectral domain. The refined signal is then indicative of the time varying intensity. A shape recognition means is then employed in the time domain for comparing the output against a predicted output or trend to provide an indication of the progress of the process.

From a still further aspect the invention consists in a process control system where a time evolving spectral output from a plasma is detected by a spectral detection means and then used in combination with the application of shape recognition techniques to provide a continuous measure of process progress against a predicted trend.

Thus in embodiments of the invention the spectral output of the plasma system is being monitored by shape recognition techniques. Filters can be established in the time, frequency and optical frequency domains which respond to particular characteristic forms. The predicted signal behaviour is examined for these characteristic forms prior to running the process yielding a data set that is indicative of process progress towards an endpoint. During the process run that is required to be automated the actual data train is interrogated by the same shape recognition filter set yielding a pointer position against the predicted behaviour which is constantly updated permitting complete access at all times to a measure of status of the etched position or other process.

While further modifications and improvements may be made without departing from the scope of this invention, the following is a description of examples of the invention, referring to the drawings, in which.

Figure 4:
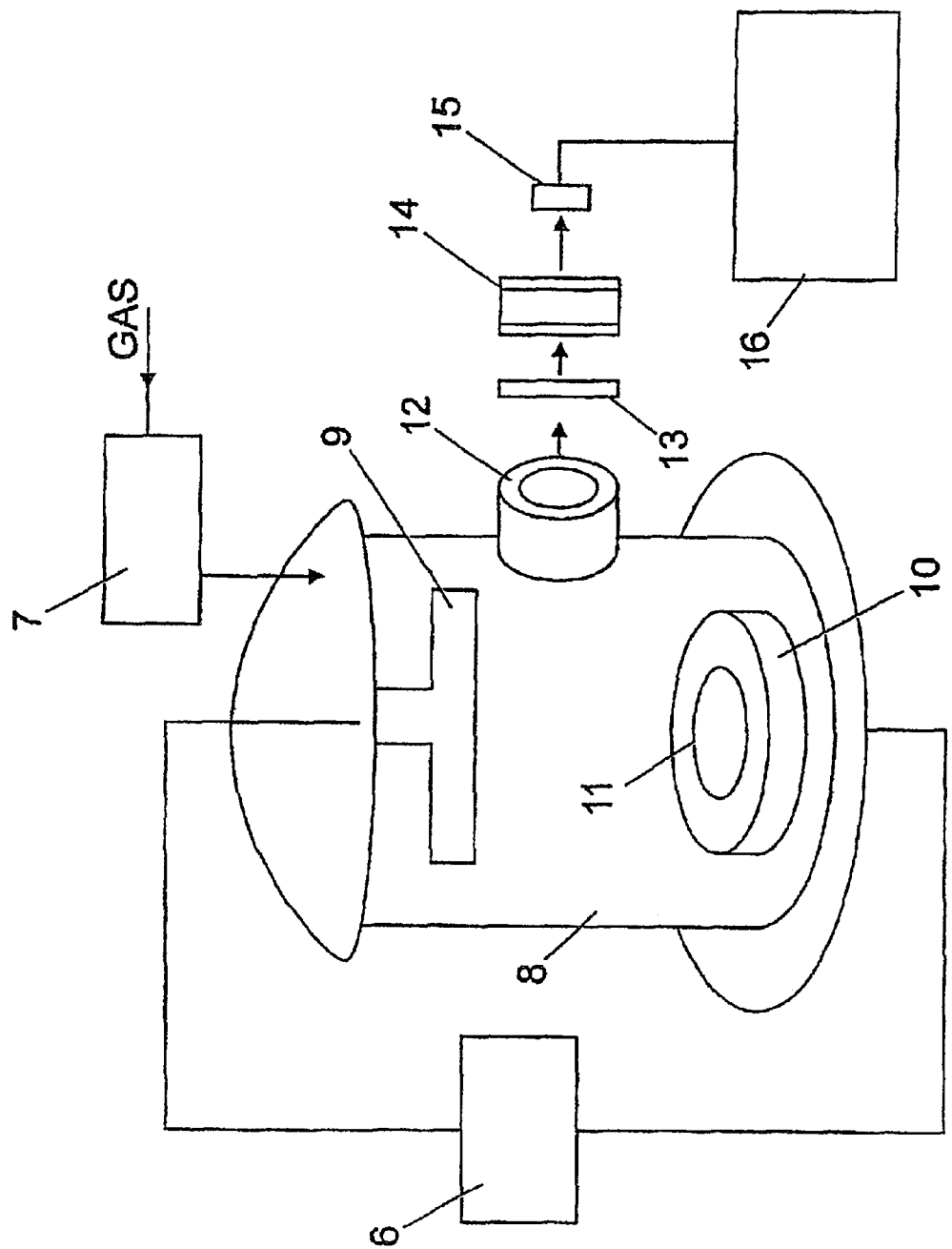
FIG. 4 is a schematic illustration of a preferred embodiment of the apparatus of the invention.

Referring particularly to FIG. 4, in a typical process a silicon substrate 11 to be etched is masked with a two-dimensional pattern of photo resist and containing within the depth of the silicon structure a buried layer of silicon oxide, in a manner well known per se. The substrate 11 is placed in a plasma reactor system comprising a vacuum vessel 8 which is provided with vacuum pumping means (not shown) and electrodes 9 and 10. The substrate 11 is placed close to or on one of the electrodes 9, 10.

The etch system is provided with a plasma excitation means 6 and a gas control means 7. In the preferred embodiment at least one of these is pulsed so as to provide a cyclically varying environment in the vacuum chamber 8.

A window 12 allows optical radiation from the plasma to be incident on a mechanism which is provided for computing a particular spectral line of the plasma emission and consisting of a thin film filter 13 which is followed by 'Fabry-Perot' etalon 14 that has been suitably adjusted to isolate radiation that shows cyclical behaviour characteristics of the particular process. The output of 'Fabry-Perot' etalon 14 is incident on a detector means 15 which produces an output indicative of the instantaneous intensity of the selected spectral frequency. The detector means 15 then passes its output signal to a signal processing means 16 within which shape recognition algorithms analyse the signal and produce a control signal to indicate when a predetermined event has occurred or to produce a continuous report on the progress of the process.

Figure 1:
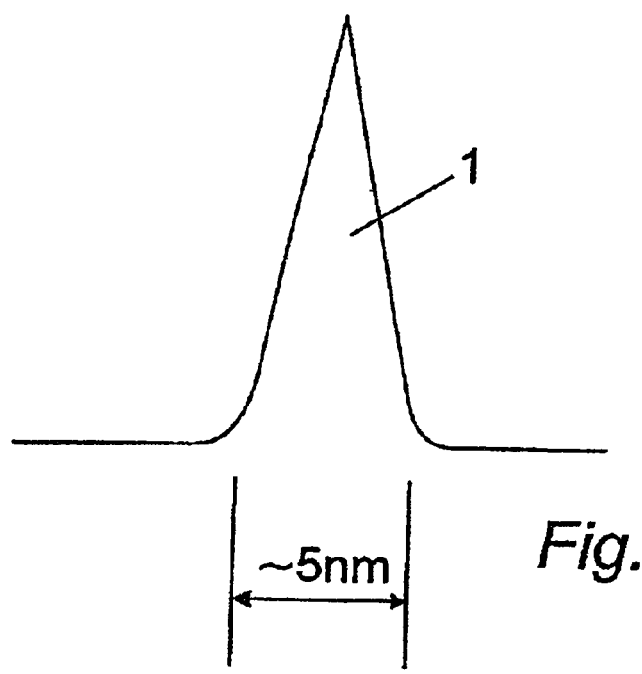
FIG. 1 shows the typical optical transmission of a thin film filter.

As seen in FIG. 1, the narrow band filter 13 provides a convenient means for isolating a particular spectral line but in general it is not precise enough in its response to isolate a particular line to the exclusion of other lines that may interfere with it. The typical band pass 1 of such a filter is approximately 5 nanometers.

Figure 2:
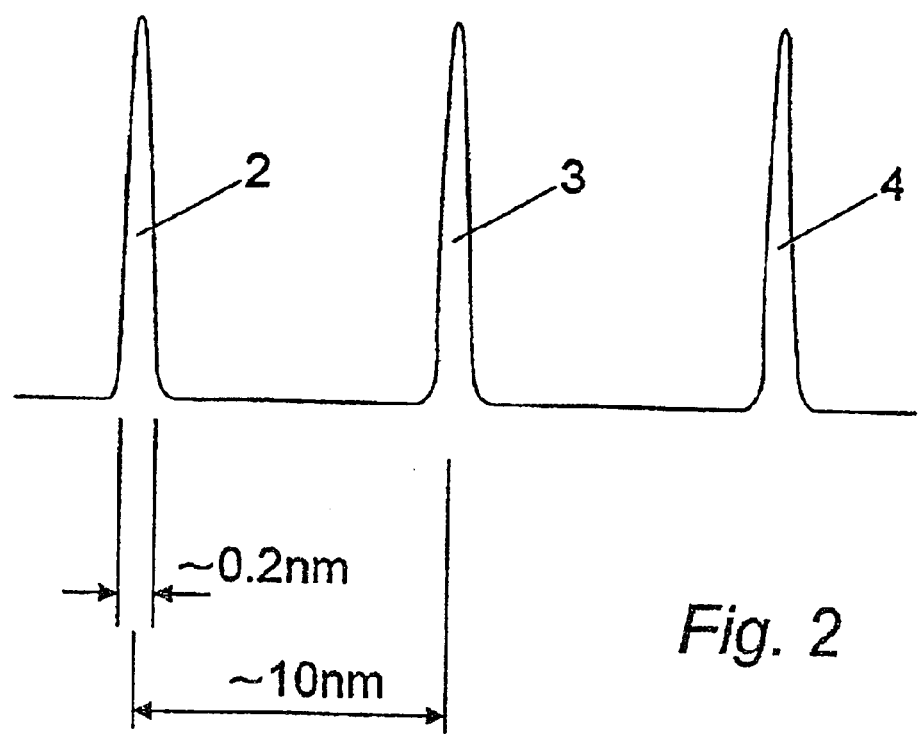
FIG. 2 shows the typical optical transmission of a 'Fabry-Perot' etalon.

The 'Fabry-Perot' etalon 14 on the other hand, as seen in FIG. 2, provides a very sharp spectral response but also allows adjacent sharp responses which are relatively close in frequency terms. The individual optical passbands are typically very narrow at about 0.2 nanometer but there is a multiplicity of them separated at typically 10 nanometers.

Figure 3:
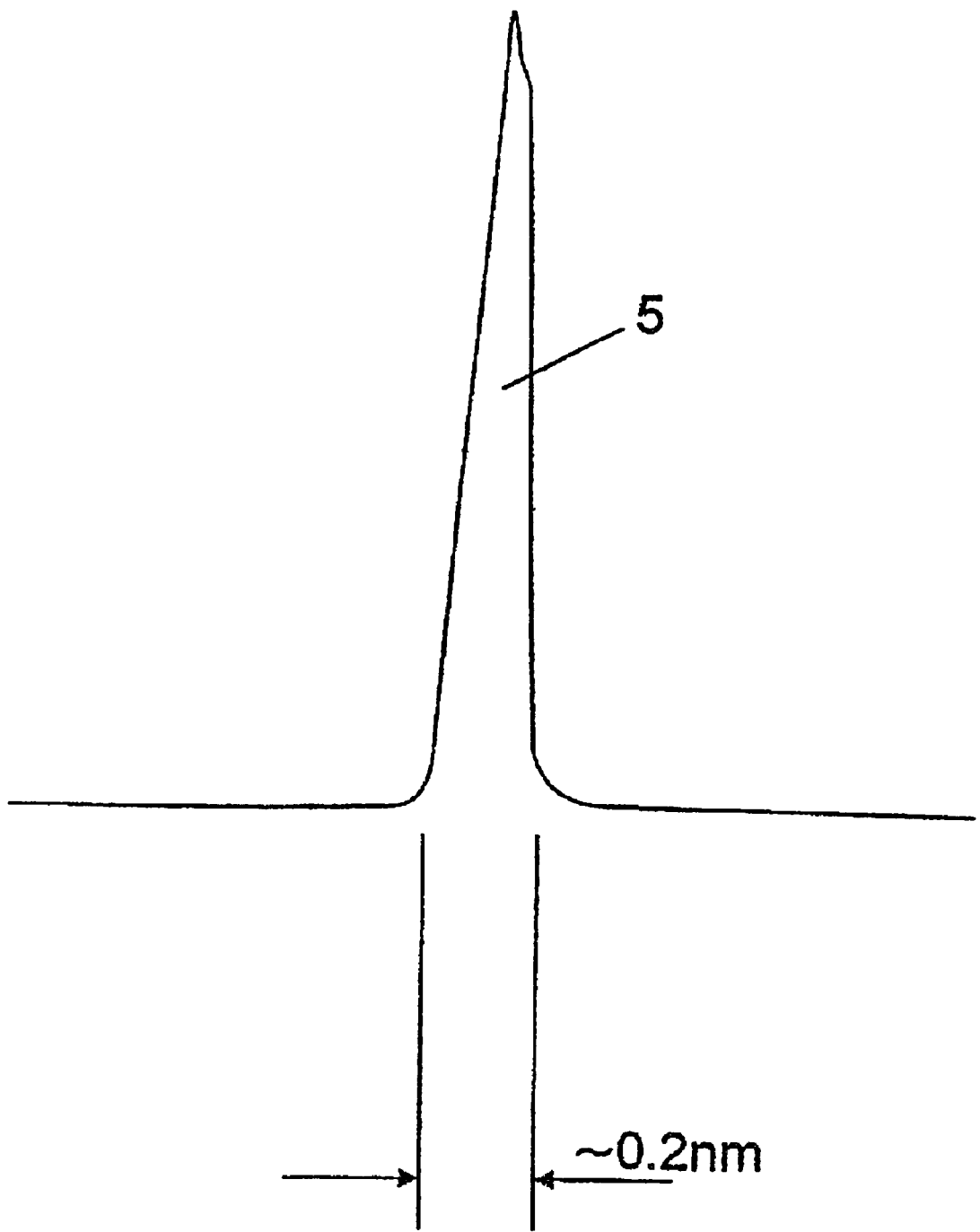
FIG. 3 shows the typical optical transmission of the combination of a thin film filter with a 'Fabry-Perot' etalon.

The combination of the two elements, FIG. 3, provides a means for convenient isolation of particular spectral lines. With suitable angle tuning of the 'Fabry-Perot' etalon, a single narrow passband is obtained at a frequency characteristic of the etch process being monitored.

Suitable thin film filters and 'Fabry-Perot' etalons will be readily apparent to those skilled in the art. As one example, suitable elements are those available from Melles Griot Technical Optics Limited of Onchan, Isle of Man. Likewise, the detector may be any detector suitable to handle the optical output; as one example, we have used a photomultiplier tube by Hamamatsu.

Gaseous precursors are chosen so that with one particular concentration of components and with particular levels and bias of Radio Frequency or microwave power the silicon material is etched. With reference to the cyclic etch/passivation method of forming features in the workplace, the etch and passivation steps are discrete; see for example published PCT application WO-A-9414187, the contents of which are hereby incorporated by reference.

Figure 5:
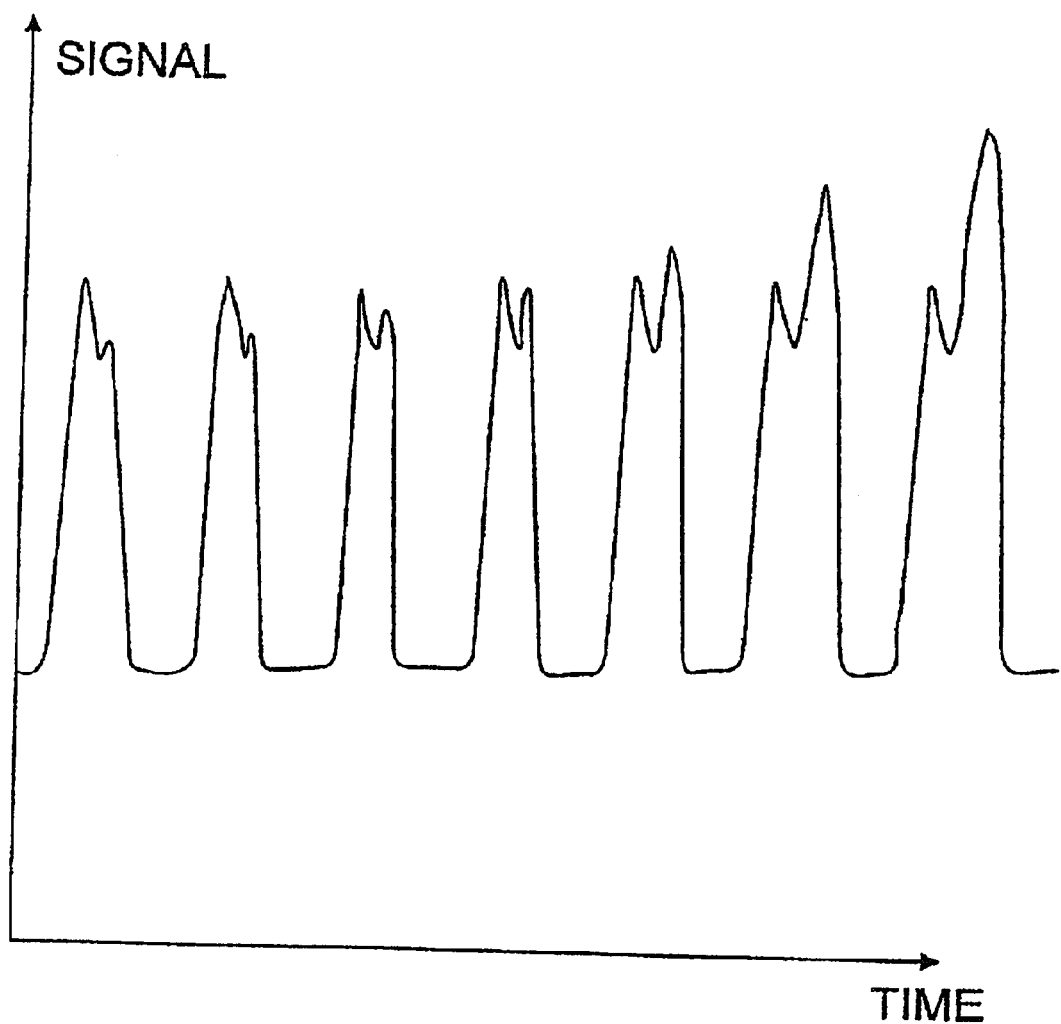
FIG. 5 shows a typical output signal from a detector of the apparatus of FIG. 4.

The output signal from the detector 15 (FIG. 5) shows a characteristic wavetrain in time consisting of repetitive double peaks. The repetitive signal is due to the cyclical nature of the process. The distinctive double peak shape is due to the etch of polymer followed by the etch of silicon. The overall signal is superimposed on noise from a variety of sources including optical noise and time jitter pulsing when a deposition/etch cycle is used. The characteristic shape of the time development of the spectral line signal is provided by an array of digital filters with impulse responses matched to the characteristics of the different time epochs. This array of filters can be progressive and examine longer time segments as the end point of the process approaches. The historical match to longer segments of characteristic signal shape increases the confidence of measure of exactly where in the process progression the etch is at any particular time.

More specific examples of the shape recognition process will now be described.

Figure 6:
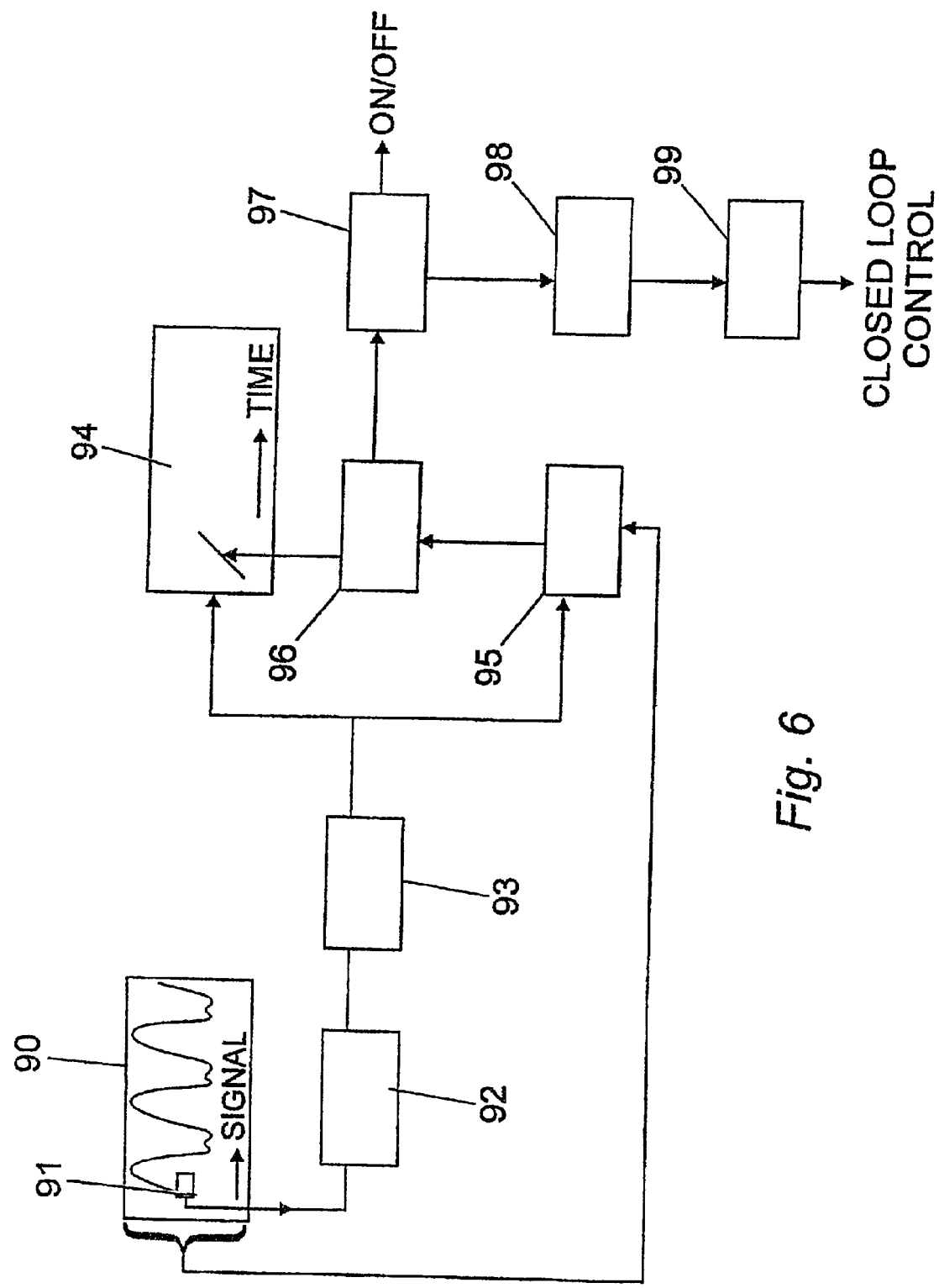
FIG. 6 is a flow chart illustrating data processing carried out in one form of the invention.

Referring to FIG. 6, which illustrates in flow-chart form the data processing carried out in the preferred embodiment, an idealised prediction of the signal obtained from the process scanned by a data window 91 which, in the preferred embodiment, may be a data window extending to 1/3000 of the data size. The contents of the data window 91 are then passed to a software routine 92 that analyses frequency. In the preferred embodiment this is a Fast Fourier Transform. The output of the Fast Fourier Transform 92 is then used to construct an adaptive digital filter 93 that passes the frequencies present as being predicted to be present in the data window 91 and highly attenuates other frequencies. The output of the digital filter 93 is recorded as the processed signal against time 94. The digital filter 93 is then used to carry out a shape recognition 95 as compared to the idealised prediction 90. In the preferred embodiment this shape recognition 95 may be accomplished by a correlation of the Fourier spectrum of the processed signal against the Fourier spectrum of the idealised signal. The output of the shape recognition 95 then yields a best match which is the parameter 96 at any point in time of the processed signal. This value is then compared to the target process condition to give a termination On/Off decision. Also this value is compared at 98 to time to give a rate signal which may be used for closed loop process control.

Figure 7:
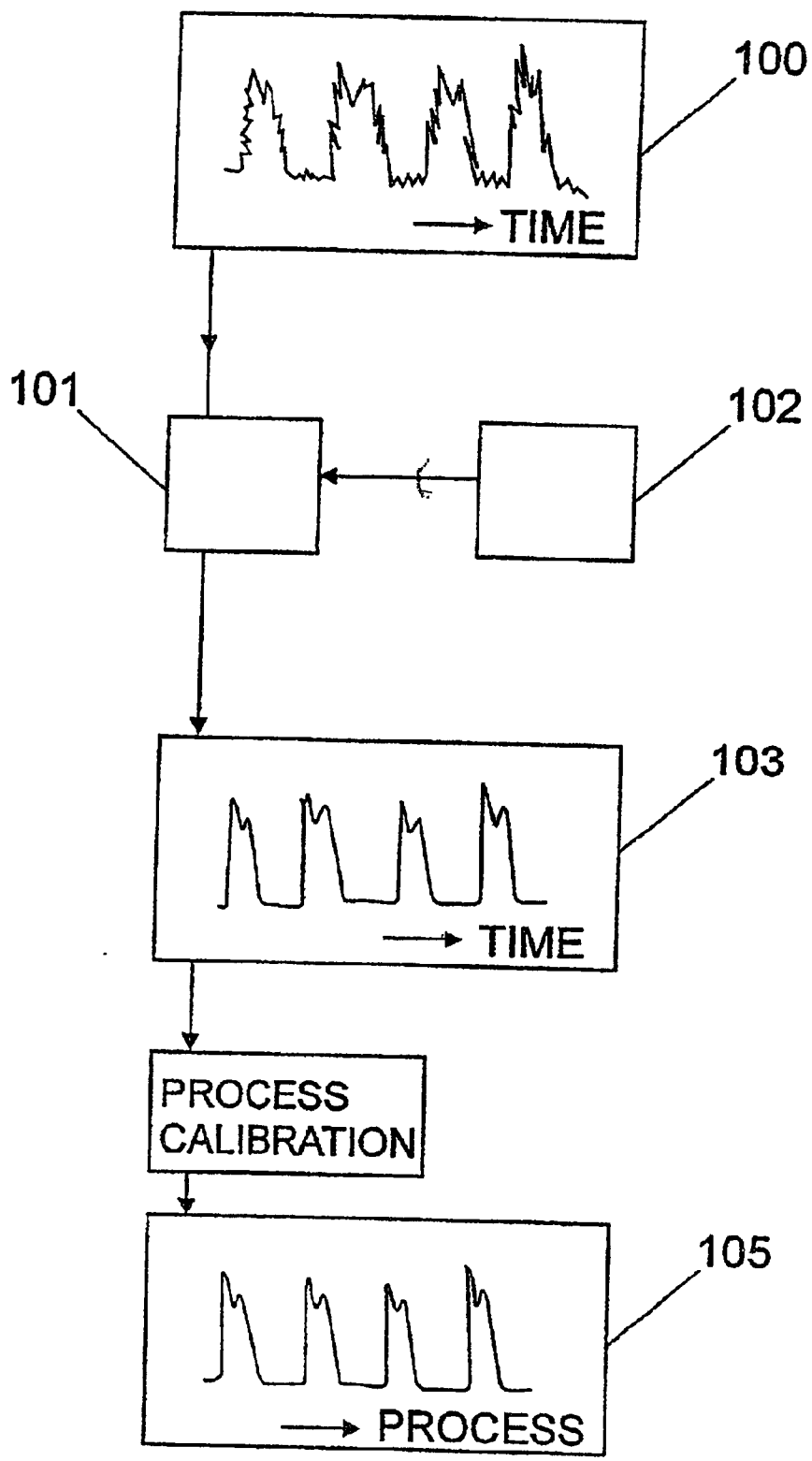
FIG. 7 illustrates an alternative embodiment of data processing.

If there is inadequate knowledge of the process to allow a full idealised signal to be produced, the shape recognition may be achieved by a calibration run. In FIG. 7 the unprocessed signal output 100 of an etch process is then processed by a digital filter 101 using filter parameters derived from keyboard entry 102. The output of the digital filter 103 is then compared to any predictive modelling or prior experience of film shape to ensure that representative features are present. This processed calibration run is then calibrated against a desired etch by an off-line technique such as stylus profiling. The resulting calibration data set 105 is then used in exactly the same way as the idealised signal data set 90 in the previous preferred embodiment.

The skilled reader will understand that the method for analysing frequencies may be of many different types such as cosine, sine or Laplacian methods. The skilled reader will also understand that the shape comparison technique may be achieved by many techniques including Laplace Transforms and Gradiometer Transforms. The data windows may also be of varying extent. The data set that is to be compared to, which may be an idealised data set resulting from a model or a calibration data set, is used in conjunction with a range of data windows. These data windows increase in length from one to the other so that if confidence of recognition of shape by a correlation technique using the Fast Fourier Transform or a Laplacian Technique, or application of any other shape recognition method such as the Gradiometer Transform, falls below a pre-defined minimum level then the subsequent increased size window may be used. Use of a data window of increased size has the advantage of allowing more data to be used to recognise features. It has the concomitant disadvantage that more data has to be present in the processed data stream to allow a meaningful comparison but, since the movement to a larger data window only occurs after more processed data has been already collected, this disadvantage has no impact on the availability of process data. Under circumstances where it is desirable for the confidence of fit to be very high, it may be desirable to use data windows only varying by a very small amount from each other and to automatically change from one data window to the subsequent one rather than waiting for an inadequate fit to be recorded.

It should be understood that although the example cited is that for cyclic (etch/passivation) etching of silicon, other materials can be etched or other plasma process performed under the control of the present method and system.

The advantages of the invention are that the use of shape recognition techniques automates the plasma process allowing for unattended operating and the rapid commissioning of process. A further advantage of the technique is that use of the shape and trend of the curve as opposed to traditional level discrimination increases the immunity of the measurement to noise source including shot to shot noise arising from time jitters in a pulsed process. A further advantage of the technique is that the shape recognition method yields a confidence of fit at all points along a predicted curve which in addition to endpoint detection provides measures which can be used for continuous optimisation of the process parameters.

A further advantage is that light from the plasma can be obtained at a wide variety of locations, so the system does not inhibit chamber design. Indeed, the input for the filter 13 could be brought from the chamber in an optical fibre.

Instead of using the spectral emission of the plasma, it is possible to use the spectral absorption by the plasma or by reaction species or product species of a defined light source, such as a frequency swept laser. This is used to produce a time-varying signal, which is analysed in the same way.

Figure 8:
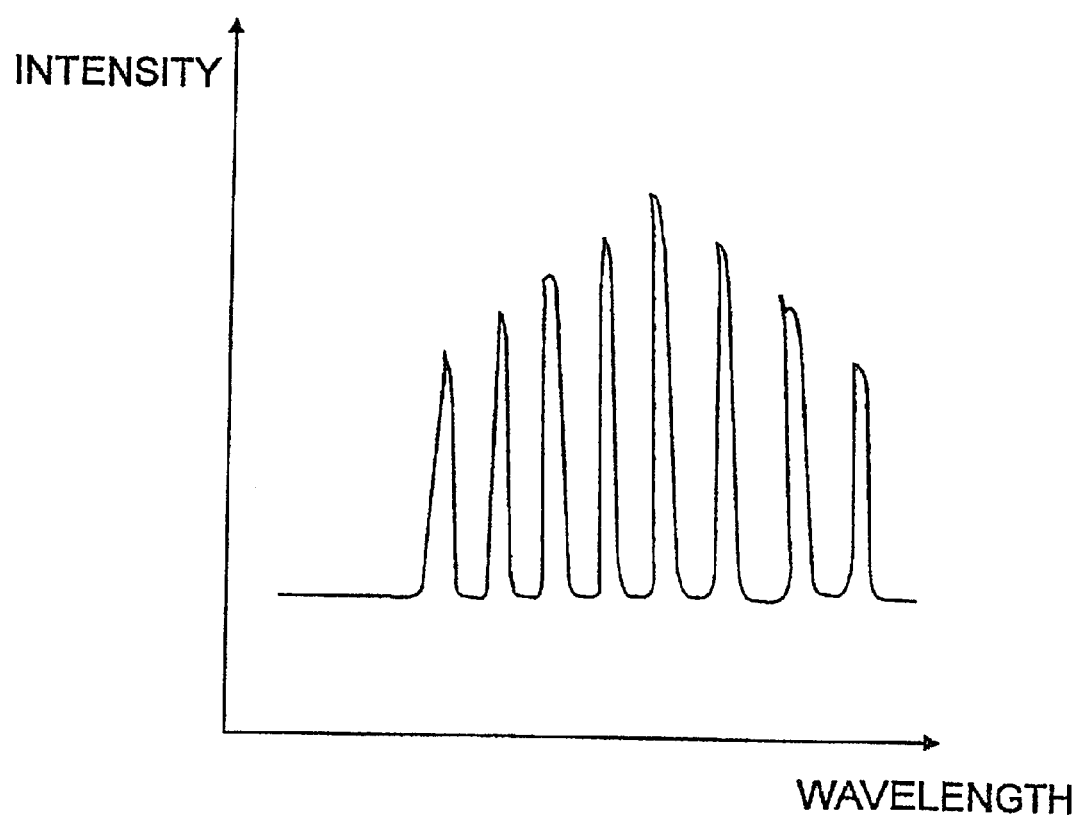
FIG. 8 is a graph illustrating a modified application of the invention.

As a further example of the invention if the spectral output that is characteristic of the process development is not an atomic spectral line (FIG. 8) but rather a vibrationally broadened molecular series of lines then a particular example of the use of shape recognition techniques in the spectral domain is to search for the existence of this species by the use of an element which responds to the characteristic form. A vibrationally broadened molecular series has a spacing which is characteristic and constant in wavenumbers. Conveniently the 'Fabry-Perot' etalon has a series of passbands which are also linearly separated in wavenumbers. Therefore a specifically designed 'Fabry-Perot' etalon conveniently implements the shape recognition technique in hardware rather than software.

Figure 9:
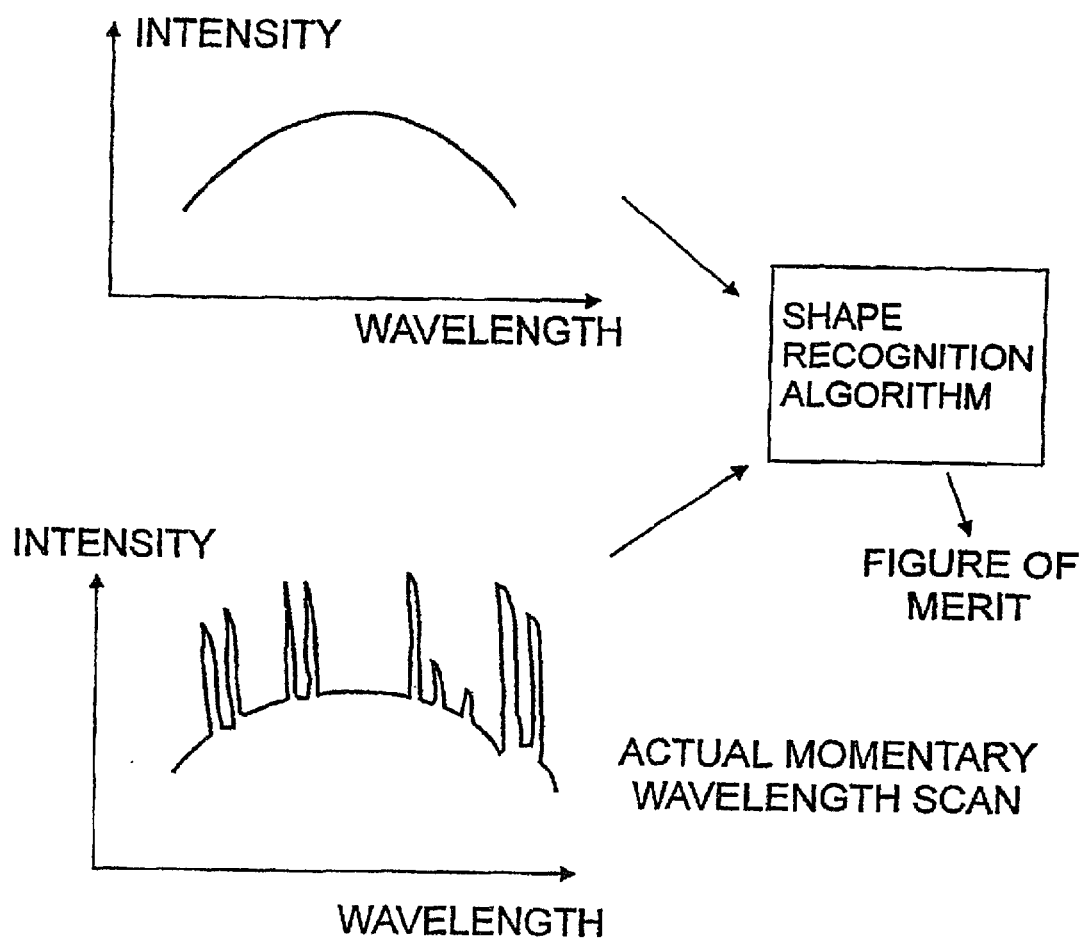
FIG. 9 illustrates graphically a further modification.

As a further example of the invention if the spectral output that is characteristic of the process development is as a result of chemical reaction between reactants produced as by-products of the main plasma process then such chemiluminescent spectral output is likely to form a broad continuum spectral feature. A convenient implementation of the shape recognition technique (FIG. 9) in the spectral domain is to take a rapid wide-band spectral measurement and then apply a shape recognition algorithm in the spectral domain which algorithm is derived from the specific envelope function form characteristic of the wide band chemiluminescent signal of the particular reaction that is required to be monitored. Such an approach allows strong signals derived from specific plasma processes to be eliminated prior to examination of the signal for its time behaviour.

What is claimed is:

1. A method for automatically determining the progress of a process, said process being one based upon the use of a plasma which exhibits a changing spectral characteristic as the process progresses, said spectral characteristic being selected from the group consisting of absorption and radiation; the method comprising:
   continuously monitoring at least part of said spectral characteristic to provide a spectral signal, and
   electronically applying shape recognition techniques to the shape of said signal.

2. The method of claim 1, in which said shape recognition techniques are applied to the shape of said signal in the time domain.

3. The method of claim 2, further including the preliminary step of applying shape recognition techniques to said spectral characteristics in the optical frequency domain.

4. The method of claim 1, in which the shape recognition is achieved by digital filtering.

5. The method of claim 1, in which the shape recognition is achieved by a series of masks derived from different time epochs.

6. The method of claim 5, in which said series of masks is derived using a method selected from the group comprising a Gradiometer transform, a Fourier transform, a Laplace transform, a Kohonen self-organising map, a cellular neural network paradigm, polynomial interpolated measures, and fractals.

7. A process control system for automatically determining the progress of a process, said process being one based upon the use of a plasma which exhibits a changing spectral characteristic as the process progresses, said spectral characteristic being selected from the group consisting of absorption and radiation, the system comprising:

monitoring means for continuously monitoring at least part of said spectral characteristic to provide a spectral signal, and shape recognition means for applying shape recognition techniques to the shape of said signal to compare said signal with a predicted output to provide a measure of the progress of the process.

8. The system of claim 7, in which said shape recognition means comprises digital filtering means operating upon said signal in the time domain.

9. The system of claim 8, in which said monitoring means includes spectral detection means adapted to perform shape recognition on said spectral characteristic in the optical frequency domain.

* * * * *